(12) United States Patent
Ahn et al.

(10) Patent No.: US 10,309,961 B2
(45) Date of Patent: Jun. 4, 2019

(54) BIO-SENSING DEVICE

(71) Applicant: NDD, INC., Gyeongsangbuk-do (KR)

(72) Inventors: Sae Young Ahn, Gyeongsangbuk-do (KR); Hyun Hwa Kwon, Gyeongsangbuk-do (KR)

(73) Assignee: NDD, INC., Gyeongsangbuk-Do (KR)

( * ) Notice: Subject to any disclaimer, the term of this patent is extended or adjusted under 35 U.S.C. 154(b) by 59 days.

(21) Appl. No.: 15/473,751

(22) Filed: Mar. 30, 2017

(65) Prior Publication Data

US 2017/0285017 A1  Oct. 5, 2017

(30) Foreign Application Priority Data

Mar. 31, 2016 (KR) .................. 10-2016-0039183

(51) Int. Cl.
| | | |
|---|---|---|
| *G01N 27/00* | (2006.01) | |
| *G01N 33/543* | (2006.01) | |
| *H01L 27/28* | (2006.01) | |
| *H01L 51/00* | (2006.01) | |
| *H01L 51/05* | (2006.01) | |
| *G01N 27/414* | (2006.01) | |

(52) U.S. Cl.
CPC ..... *G01N 33/5438* (2013.01); *G01N 27/4145* (2013.01); *H01L 27/283* (2013.01); *H01L 51/0048* (2013.01); *H01L 51/0541* (2013.01); *H01L 51/0562* (2013.01)

(58) Field of Classification Search
CPC ............ G01N 33/5438; G01N 27/4145; H01L 51/0562; H01L 51/0048; H01L 27/283; H01L 51/0541
See application file for complete search history.

(56) References Cited

U.S. PATENT DOCUMENTS

| | | | |
|---|---|---|---|
| 2014/0299922 A1 | 10/2014 | Shi et al. | |
| 2014/0335629 A1* | 11/2014 | Ahn | G01N 27/4146 436/501 |

FOREIGN PATENT DOCUMENTS

| | | |
|---|---|---|
| CN | 101287986 A | 10/2008 |
| CN | 103235022 A | 8/2013 |
| KR | 1020140132869 A | 11/2014 |
| KR | 1020110116461 | 10/2016 |
| KR | 1020150111395 A | 10/2016 |

\* cited by examiner

*Primary Examiner* — Dennis White
(74) *Attorney, Agent, or Firm* — Stuart H. Mayer; Mayer & Williams PC

(57) ABSTRACT

The present invention provides a bio-sensing device. The bio-sensing device includes an array of unit cells, each unit cell including: a source electrode and a drain electrode spaced apart from each other; a sensing film that serves as a channel between the source electrode and the drain electrode; and gate electrodes spaced apart from the sensing film, wherein the gate electrodes is disposed at a lower level than the source electrode, the drain electrode and the sensing film.

16 Claims, 3 Drawing Sheets

BIO-SENSING DEVICE

CROSS-REFERENCE TO RELATED APPLICATIONS

This application claims priority to and the benefit of Korean Patent Application No. 10-2016-0039183 filed in the Korean Intellectual Property Office on Mar. 31, 2016, the entire contents of which are incorporated herein by reference.

BACKGROUND

Field

The present invention relates to a bio-sensing device, and more particularly, to a bio-sensing device having an electrode structure.

Related Technology

The test method used for the diagnosis of diseases is mainly based on coloration, fluorescence, etc. by enzyme reaction, but recently, immunoassay using immunity reaction between antigen and antibody has also been used. In the conventional immunoassay, the optical measurement method combining the optical label with the catalytic reaction of the enzyme was the most used. These methods have disadvantages in that they require a complicated procedure that can be performed mainly by a laboratory-oriented and skilled researcher, the apparatus for analysis is large and expensive, and the analysis takes a long time.

Such a method has been disclosed in Korean Patent Application Publication No. 2011-0116461A (published on Oct. 26, 2011, title of the invention: Diagnostic Apparatus for Immunoassay and Immunoassay Method Using the Same)

SUMMARY

The present invention has been made to solve a lot of problems including the above ones, by providing a bio-sensing device that is capable of shortening analysis time and is relatively inexpensive. However, these problems are for illustrative purposes only, and the scope of the present invention is not limited thereto.

There is provided a bio-sensing device according to an aspect of the present invention in order to solve the above-described problems. The bio-sensing device includes an array of unit cells, each unit cell including: a source electrode and a drain electrode spaced apart from each other; a sensing film that serves as a channel between the source electrode and the drain electrode; and gate electrodes spaced apart from the sensing film, wherein the gate electrodes is disposed at a lower level than the source electrode, the drain electrode and the sensing film.

In the bio-sensing device, the material of the sensing film may include carbon nanotube (CNT), graphene, molybdenum disulfide (MoS2), or phosphorene. Here, a part of the source electrode or the drain electrode in contact with the carbon nanotubes, graphene, molybdenum disulfide, or phosphorene may have a comb-like shape.

In the bio-sensing device, the unit cell may further include a receptor that is attached to the sensing film and capable of binding to a target material.

In the bio-sensing device, the sensing film may be made of a material that can vary in resistance depending on the receptor and a target material bound to the receptor, the receptor may be attached to the sensing film by a functional group and is any one or more selected from the group consisting of an enzyme substrate, a ligand, an amino acid, a peptide, an aptamer, a protein, guanine, a nucleic acid, a lipid and a carbohydrate, the functional group may be at least one selected from the group consisting of an amine group, a carboxyl group, a thiol group and a lipid, and the target material may be at least one selected from the group consisting of a protein, a peptide, an aptamer, a nucleic acid, an oligosaccharide, an amino acid, a carbohydrate, a dissolved gas, a sulfur oxide gas, a nitrogen oxide gas, sodium (Na) or sodium ions, potassium (K) or potassium ions, a residual pesticide, a heavy metal and an environmentally harmful substance.

The bio-sensing device may further include an upper substrate on which the source electrode, the drain electrode, and the sensing film are formed; and a lower substrate on which the gate electrode is formed, wherein the upper substrate and the lower substrate are vertically stacked and connected to each other.

In the bio-sensing device, the unit cell may further include an insulating member interposed between the sensing film and the gate electrode, and the surface of the insulating member may be subjected to plasma treatment to improve the adhesion between the insulating member and the sensing film.

In the bio-sensing device, the unit cell may include an insulating member interposed between the sensing film and the gate electrode, and a buffer layer interposed between the insulating member and the sensing film to improve adhesion.

In the bio-sensing device, the unit cell may be a multichannel structure with the sensing film including a first sensing film, to which a first receptor capable of binding to a first target material may be attached, and a second sensing film, to which a second receptor capable of binding to a second target material may be attached.

In the bio-sensing device, the unit cells may be repeatedly arrayed.

Advantageous Effects

According to the embodiments of the present invention as described above, it is possible to provide a bio-sensing device that is capable of shortening analysis time and is relatively inexpensive. Of course, the scope of the present invention is not limited by these effects.

DETAILED DESCRIPTION

Figure 1:
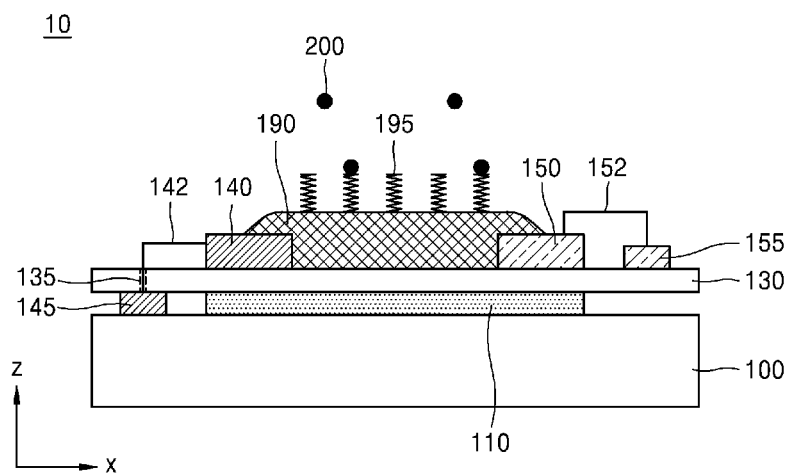
FIG. 1 is a schematic view illustrating a cross section of a unit cell constituting a bio-sensing device according to an embodiment of the present invention.

Hereinafter, embodiments of the present invention will be described in detail with reference to the accompanying drawings. In the specification, it will be understood that when an element, such as a layer, region, or substrate, is referred to as being "on," "connected to," "stacked on" or "coupled to" another element, it can be directly "on," "connected to," "stacked on" or "coupled to" the other element or intervening elements may be present. In contrast, when an element is referred to as being "directly on," "directly connected to" or "directly coupled to" another element, there are no intervening elements present.

In the drawings, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. Furthermore, the thickness and size of each layer in the drawings may be exaggerated for convenience and clarity of explanation. Like numerals refer to like elements.

Figure 2:
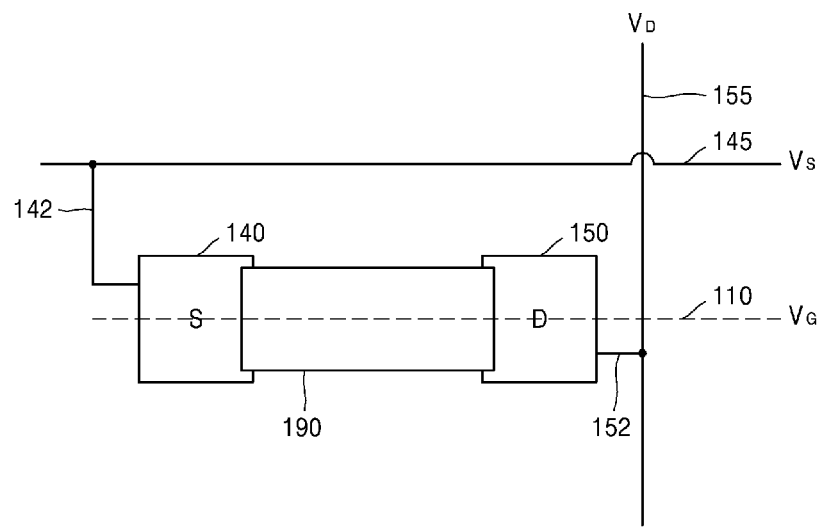
FIG. 2 is a circuit diagram schematically illustrating a circuit structure of a unit cell constituting the bio-sensing device according to an embodiment of the present invention.

FIG. 1 is a schematic view illustrating a cross section of a unit cell constituting the bio-sensing device according to an embodiment of the present invention, and FIG. 2 is a circuit diagram schematically illustrating a circuit structure of a unit cell constituting the bio-sensing device according to an embodiment of the present invention.

Referring to FIGS. 1 and 2, a bio-sensing device according to an embodiment of the present invention includes a unit cell 10 arranged in an array. The unit cell 10 includes a source electrode 140 and a drain electrode 150 spaced apart from each other, a sensing film 190 that serves as a channel between the source electrode and the drain electrode, and gate electrodes 110 and 160 spaced apart from the sensing film.

The unit cell 10 includes a receptor 195 that is attached to the sensing film 190 and capable of binding to a target material 200. The receptor 195 may be attached to the sensing film 190 by a functional group. For example, the receptor 195 may be any one or more selected from the group consisting of an enzyme substrate, a ligand, an amino acid, a peptide, an aptamer, guanine, a protein, a nucleic acid, a lipid and a carbohydrate. Meanwhile, the functional group may be at least one selected from the group consisting of, for example, an amine group, a carboxyl group, a thiol group and a lipid. The target material 200 may be selected from the group consisting of, for example, a protein, an aptamer, a peptide, a nucleic acid, an oligosaccharide, an amino acid, a carbohydrate, a dissolved gas, a sulfur oxide gas, a nitrogen oxide gas, sodium (Na) or sodium ions, potassium (K) or potassium ions, a residual pesticide, a heavy metal and an environmentally harmful substance.

The sensing film 190 may be made of a material that can vary in resistance depending on the receptor 195 and a target material 200 bound to the receptor. The material of the sensing film 190 may include, for example, carbon nanotube (CNT), graphene, molybdenum disulfide (MoS2), or phosphorene. Meanwhile, in the bio-sensing device according to a modified embodiment of the present invention, the sensing film 190 may be made of a material that can vary in resistance by reacting directly with the target material 200 without interposing the receptor 195.

The gate electrode 110 is disposed at a lower level than the source electrode 140, the drain electrode 150 and the sensing film 190. That is, the level at which the gate electrode 110 is located is lower than the level at which the source electrode 140, the drain electrode 150, and the sensing film 190 are located. In this specification, a level is a term for distinguishing the vertical positional relationship in the cross section shown in FIG. 1.

The unit cell 10 constituting the bio-sensing device according to an embodiment of the present invention includes insulating members 130 interposed between the sensing film 190 and the gate electrode 110. The insulating member 130 may have the form of, for example, an insulating film or an insulating substrate.

The surface of the insulating member 130 may be subjected to plasma treatment to improve the adhesion between the insulating member 130 and the sensing film 190. Alternatively, a buffer layer (not shown) may be interposed between the insulating member 130 and the sensing film 190 to improve adhesion.

Meanwhile, drain wiring lines 155 electrically connected to the drain electrode 150 are arranged to be spaced from each other while extending in parallel in the first direction on the upper layer. Source wiring lines 145 electrically connected to the source electrode 140 are arranged to be spaced apart from each other while extending in parallel in the second direction on the lower layer where the gate electrodes 110 are disposed. The first direction and the second direction are not parallel to each other, and may be, for example, perpendicular to each other. The gate electrodes 110 may be commonly connected, and the drain wiring lines 155 or the source wiring lines 145, respectively, may be commonly connected.

The bio-sensing device according to an embodiment of the present invention can be used as an inspection device that is used for disease diagnosis and can be used as a sensing device that uses an immune reaction between an antigen and an antibody depending on the kind of a sensing film and a receptor. In this case, it is advantageous that, since the result of electrical measurement is utilized, a complicated procedure is not required in the analysis process, the apparatus for analysis is relatively inexpensive, and the analysis does not take a long time.

The embodiment shown in FIG. 1 may be extended to provide a plurality of unit cells 10 per substrates 100 and 130. For example, if the size of the unit cell 10 is further reduced to nano size, the number of unit cells 10 on the substrates 100 and 130 may be, for example, 96, 384, 1536, 6144, 24576, 98304, and 393216, respectively. Thus, by increasing the number of unit cells per substrate, the bio-sensing device of the present invention is capable of diagnosing various diseases and drastically reducing the inspection cost due to the shortened inspection time.

Figure 3:
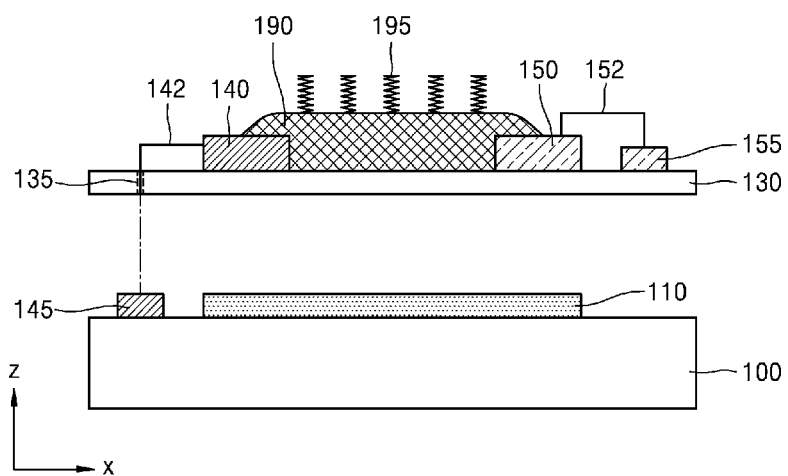
FIG. 3 is a view illustrating an example of manufacturing a unit cell constituting the bio-sensing device according to an embodiment of the present invention.

FIG. 3 is a view illustrating an example of manufacturing a unit cell constituting the bio-sensing device according to an embodiment of the present invention.

Referring to FIG. 3, in order to provide the unit cell structure of FIG. 1, a lower structure having the source wiring lines 145 and the gate electrode 110 formed on the lower substrate 100 is prepared. Then, an upper structure having the drain wiring lines 155 formed on the upper substrate 130 is prepared. Then the upper structure is stacked on and connected to the lower structure. The lower substrate 100 of the lower structure may also serve as a support for the bio-sensing device. The upper substrate 130 may also serve to insulate the sensing film 190 from the gate electrode 110 and may include a through-hole 135 through which a connection pattern 142 for electrically connecting the source electrode 140 and the source wiring line 145 may pass. The upper substrate 130 may be a PCB substrate or a thin-film flexible substrate having a thickness of about 0.1 mm, and the lower substrate 100 may be a PCB substrate or a thin-film flexible substrate having a thickness of about 1 mm. The bio-sensing device according to an embodiment of the present invention can easily provide a complicated gate electrode structure at a relatively low cost by employing the above-described double substrate structure.

Figure 4:
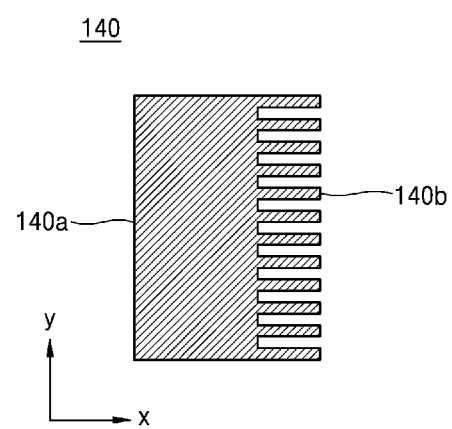
FIG. 4 is a schematic view illustrating a shape of a source electrode in a unit cell constituting the bio-sensing device according to an embodiment of the present invention.

FIG. 4 is a view illustrating a shape of a source electrode in a unit cell constituting the bio-sensing device according to an embodiment of the present invention.

Referring to FIG. 4, in the source electrode 140, a region 140b in contact with the sensing film 190 such as carbon nanotubes, graphene, molybdenum disulfide, or phosphorene may have a comb-like shape. According to this structure, the bonding force or interconnectivity between the sensing film 190 and the source electrode 140 can be improved. Likewise, in the drain electrode, a region in contact with the sensing film such as carbon nanotube or graphene may have a comb-like shape, thereby improving the bonding force or interconnectivity between the drain electrode and the sensing film.

Figure 5:
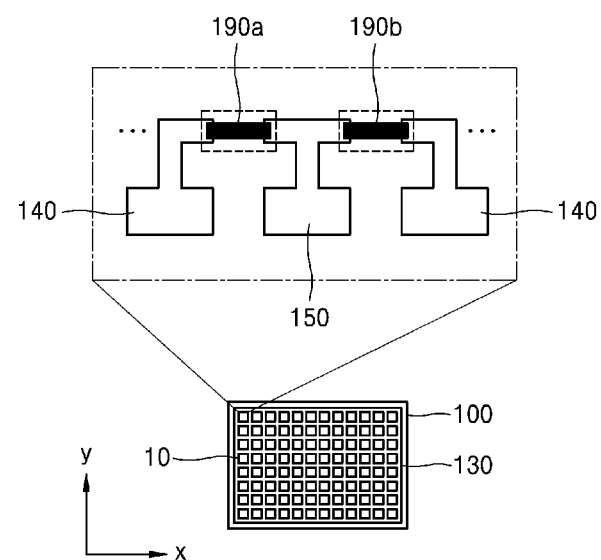
FIG. 5 is a schematic view illustrating a bio-sensing device and a unit cell constituting the bio-sensing device according to another embodiment of the present invention.

FIG. 5 is a schematic view illustrating a bio-sensing device and a unit cell constituting the bio-sensing device according to another embodiment of the present invention. The bio-sensing device according to another embodiment of the present invention is a multi-channel connection structure including at least two sensing films.

Referring to FIG. 5, the bio-sensing device according to another embodiment of the present invention includes a sensing film which is an extension of the sensing film in the unit cell shown in FIG. 1. In this embodiment, the sensing film may include a first sensing film 190a, to which a first receptor capable of binding to a first target material may be attached, and a second sensing film 190b, to which a second receptor capable of binding to a second target material may be attached. The first sensing film 190a is a channel between the source electrode 140 shown on the left side and the drain electrode 150, and the second sensing film 190b is a channel between the source electrode 140 shown on the right side and the drain electrode 150. Although not shown in the drawing, the gate electrode is disposed at a lower level than the source electrode 140, the drain electrode 150, the first sensing film 190a, and the second sensing film 190b.

The bio-sensing device having the above-described multi-channel connection structure can be applied to, for example, a glycated protein measurement sensor. In this case, a specific illustrative configuration will be described.

The first receptor may be disposed on the first sensing film 190a. The first receptor, which is a ligand composition, may bind to a glycated protein, which is the first target material, and serve to attach the glycated protein to the first sensing film 190a. The first receptor may include an aromatic boronic acid as an active ingredient. Particularly, the first receptor may be a material including at least one of phenylboronic acid, naphthalene boronic acid, phenanthrene boronic acid, pyrene boronic acid and anti-gHSA albumin. The glycated protein may be any one of glycated human serum albumin (gHSA), glycated IgG, and glycated IgM.

The second receptor may be disposed on the second sensing film 190b. The second receptor may bind to the glycated protein, which is the first target material and the protein, which is the second target material, and serve to attach the glycated protein and the protein to the second sensing film 190b. The second receptor may be selected from the group consisting of an enzyme substrate, a ligand, an amino acid, a peptide, a protein, a nucleic acid, a lipid and a carbohydrate, and may preferably be thyroxine. The protein may be any one of human serum albumin (HSA), IgG, and IgM.

The glycated protein present in human saliva may bind to the first receptor, which is a ligand composition, and adhere onto the first sensing film 190a, thereby changing the value of current flowing in the first sensing film 190a. That is, the first sensing film 190a may be connected with the glycated protein via the first receptor to induce the change in current in the first sensing film 190a. In addition, the protein and the glycated protein present in human saliva may bond to the second receptor and adhere onto the second sensing film 190b, thereby changing the value of current flowing in the second sensing film 190b. Therefore, the amount of current flowing in the first sensing film 190a or the second sensing film 190b may vary depending on the amount of glycated protein or protein contained in a predetermined detection solution (i.e., saliva).

In order to describe a bio-sensing device having a multi-channel connection structure, a two-channel structure has been illustrated in FIG. 5, but the technical idea of the present invention is not limited to such but may extend to three-channel, four-channel, five-channel structures, or even 20-channel structure. The bio-sensing device having such a multi-channel structure can be utilized as a device for diagnosing heart disease or cancer as well as measuring glycated proteins.

While the present invention has been particularly shown and described with reference to embodiments shown in the drawings, it is only for illustrative purposes. It will be understood by those skilled in the art that various modifications and equivalent embodiments may be made. Therefore, the scope of the present invention should be determined by the technical idea of the appended claims.

The invention claimed is:

1. A bio-sensing device comprising:
an array of unit cells, each unit cell including:
a source electrode and a drain electrode spaced apart from each other;
a sensing film that serves as a channel between the source electrode and the drain electrode;
a gate electrode spaced apart from the sensing film;
an upper substrate on which the source electrode, the drain electrode, and the sensing film are formed; and
a lower substrate on which the gate electrode is formed, wherein the upper substrate and the lower substrate are vertically stacked and connected to each other, and
wherein the gate electrode is disposed between the upper substrate and the lower substrate.

2. The bio-sensing device of claim 1,
wherein the material of the sensing film includes carbon nanotube (CNT), graphene, molybdenum disulfide (MoS2), or phosphorene.

3. The bio-sensing device of claim 2,
wherein a part of the source electrode or the drain electrode in contact with the carbon nanotubes, graphene, molybdenum disulfide, or phosphorene has a comb-like shape.

4. The bio-sensing device of claim 1,
wherein the unit cell further includes a receptor that is attached to the sensing film and capable of binding to a target material.

5. The bio-sensing device of claim 4,
wherein the sensing film is made of a material that can vary in resistance depending on the receptor and a target material bound to the receptor, wherein the receptor is attached to the sensing film by a functional group and is any one or more selected from the group consisting of an enzyme substrate, a ligand, an amino acid, a peptide, an aptamer, a protein, guanine, a nucleic acid, a lipid and a carbohydrate, wherein the functional group is at least one selected from the group consisting of an amine group, a carboxyl group, a thiol group and a lipid, and wherein the target material is at least one selected from the group consisting of a protein, a peptide, an aptamer, a nucleic acid, an oligosaccharide, an amino acid, a carbohydrate, a dissolved gas, a sulfur oxide gas, a nitrogen oxide gas, sodium (Na) or sodium ions, potassium (K) or potassium ions, a residual pesticide, a heavy metal and an environmentally harmful substance.

6. The bio-sensing device of claim 1, wherein the unit cell further includes an insulating member interposed between the sensing film and the gate electrode, and wherein the surface of the insulating member is subjected to plasma treatment to improve the adhesion between the insulating member and the sensing film.

7. The bio-sensing device of claim 1, wherein the unit cell includes an insulating member interposed between the sensing film and the gate electrode, and a buffer layer interposed between the insulating member and the sensing film to improve adhesion.

8. The bio-sensing device of claim 1, wherein the unit cell is a multi-channel structure with the sensing film including a first sensing film, to which a first receptor capable of binding to a first target material may be attached, and a second sensing film, to which a second receptor capable of binding to a second target material may be attached.

9. The bio-sensing device of claim 1, wherein the unit cells are repeatedly arrayed.

10. The bio-sensing device of claim 2, wherein the unit cells are repeatedly arrayed.

11. The bio-sensing device of claim 3, wherein the unit cells are repeatedly arrayed.

12. The bio-sensing device of claim 4, wherein the unit cells are repeatedly arrayed.

13. The bio-sensing device of claim 5, wherein the unit cells are repeatedly arrayed.

14. The bio-sensing device of claim 6, wherein the unit cells are repeatedly arrayed.

15. The bio-sensing device of claim 7, wherein the unit cells are repeatedly arrayed.

16. The bio-sensing device of claim 8, wherein the unit cells are repeatedly arrayed.

* * * * *